(12) United States Patent
Kharait

(10) Patent No.: US 11,712,445 B2
(45) Date of Patent: Aug. 1, 2023

(54) COMPOSITIONS AND METHODS FOR IMPROVING GASTROINTESTINAL FUNCTION IN SUBJECTS WITH RENAL DISEASE

(71) Applicant: Sourabh Kharait, Roseville, CA (US)

(72) Inventor: Sourabh Kharait, Roseville, CA (US)

(73) Assignee: Sourabh Kharait, Roseville, CA (US)

( * ) Notice: Subject to any disclaimer, the term of this patent is extended or adjusted under 35 U.S.C. 154(b) by 77 days.

(21) Appl. No.: 17/246,433

(22) Filed: Apr. 30, 2021

(65) Prior Publication Data
US 2022/0347196 A1    Nov. 3, 2022

(51) Int. Cl.
*A61K 31/702* (2006.01)
*A61P 1/10* (2006.01)
*A61P 13/12* (2006.01)

(52) U.S. Cl.
CPC .............. *A61K 31/702* (2013.01); *A61P 1/10* (2018.01); *A61P 13/12* (2018.01)

(58) Field of Classification Search
CPC ..... A61K 31/702; A61P 1/00–18; A61P 13/12
See application file for complete search history.

(56) References Cited

U.S. PATENT DOCUMENTS

| 2012/0202753 | A1* | 8/2012 | Morrow | A23L 33/40 514/23 |
| 2016/0051600 | A1 | 2/2016 | Martín del Campo López et al. | |
| 2018/0078573 | A1* | 3/2018 | Sprenger | A23L 33/125 |
| 2018/0169122 | A1 | 6/2018 | Hennet et al. | |
| 2020/0330492 | A1 | 10/2020 | Vigsnæs et al. | |
| 2022/0273016 | A1* | 9/2022 | Barile | A23L 33/125 |

OTHER PUBLICATIONS

Xie, L-M. et al., Int. J. Clin. Exp Med, "Effects of fermentable dietary fiber supplementation on oxidative and inflammatory status in hemodialysis patients", 2015, vol. 8, No. 1, pp. 1363-1369 (Year: 2015).*

Ramos, C. I. et al., Nephrol Dial Transplant, "Effect of prebiotic (fructooligosaccharide) on uremic toxins of chronic kidney disease patients: a randomized controlled trial", 2019, vol. 34, pp. 1876-1884 (Year: 2019).*

Chou et al., "C-Reactive Protein Predicts Vascular Access Thrombosis in Hemodialysis Patients," Blood Purification, Aug. 2006, vol. 24, Issue 4, pp. 342-346.

Wang et al., "Real-Time PCR Analysis of the Intestinal Microbiotas in Peritoneal Dialysis Patients," Applied and Environmental Microbiology, Feb. 2012, vol. 78, No. 4, pp. 1107-1112.

International Search Report, regarding Application No. PCT/US22/26962, dated Sep. 14, 2022, 15 pages.

* cited by examiner

*Primary Examiner* — Bahar Craigo
(74) *Attorney, Agent, or Firm* — Sheppard Mullin Richter & Hampton LLP

(57) ABSTRACT

The present disclosure relates generally to compositions and methods for improving the consistency and regularity of a subject's bowel movements. Additionally, the compositions and methods are useful for also improving deficiencies in nutrition, deficiencies in hemoglobin, and reducing inflammation.

15 Claims, No Drawings

COMPOSITIONS AND METHODS FOR IMPROVING GASTROINTESTINAL FUNCTION IN SUBJECTS WITH RENAL DISEASE

BACKGROUND

Constipation is prevalent in patients with renal disease. Moreover, chronic constipation is common in end stage renal disease ("ESRD") patients on dialysis (both hemodialysis and peritoneal dialysis). Constipation in renal disease is due to a variety of factors. For example, use of certain medications (e.g., phosphate binders), changes in electrolyte and fluid balance, sedentary lifestyle, and comorbidities (e.g., diabetes).

Constipation increases the risk of chronic kidney disease due to higher production of gut derived toxins such as indoxyl sulfate and p-cresyl sulfate which further lead to inflammation and increased risk of cardiovascular disease. Constipation can also alter the gut microbiome due to mechanical results of retained stool contents on the colonic gut bacteria. Correspondingly, an altered microbiome can lead to deregulation of gut motility, which in turn leads to worsening of constipation and amplifies the negative effects (e.g., inflammation and cardiovascular disease). In addition, for ESRD patients, constipation can pose a bigger risk on peritoneal dialysis as it can predispose to spontaneous bacterial peritonitis.

Thus, it is important to reduce constipation and improve the gut microbiome in patients with renal disease, particularly patients with ESRD.

SUMMARY

The present disclosure, in one embodiment, provides compositions and methods for improving gastrointestinal function in patients with renal disease by reducing constipation and improving the gut microbiome.

One embodiment of the disclosure provides a method for improving the consistency of a subject's bowel movements, comprising administering to the subject an effective amount of a composition comprising one or more oligosaccharides.

In some embodiments, the oligosaccharides are human milk oligosaccharides (HMOs). Non-limiting examples of HMOs include 2'-fucosyllactose (2'-FL), 3'-sialyllactose (3'-SL), 6'-sialyllactose (6'-SL), Lacto-N-neotetraose, Lacto-N-tetraose, monofucosyllacto-N-hexaose, Lacto-N-fucopentaose (LNFP) and lacto-neotetraose (LNnT). LNFP may be selected from the group consisting of LNFP I, LNFP II, LNFP III, LNFP IV and combinations thereof.

In some embodiments, the HMOs are synthetic. In a preferred embodiment, the synthetic HMO is 2'-fucosyllactose (2'-FL). In some embodiments, at least 10%, 20%, 30%, 40%, 50%, 60%, 70%, 75%, 80%, 85%, 90% or 95% of the oligosaccharides are 2'-FL.

In some embodiments, from 0.1 g to 20 g of 2'-FL is administered to the subject each day. In some embodiments, the administered amount of 2'-FL is from 1 g to 5 g each day.

The methods of the present disclosure, in some embodiment, are beneficial for subjects that suffer from constipation. In some embodiments, the methods of the present disclosure are beneficial for subjects having a chronic kidney disease, having an end stage renal disease, and/or on dialysis, such as peritoneal dialysis, or hemodialysis.

In some embodiments, the composition is administered to the subject for at least 4, 8, 10, 12, 15, 16, 19, 20, 24, or 30 weeks.

The method of the present disclosure can result in an improvement in nutrition or inflammation markers. Non-limiting examples of such markers include serum albumin, C-reactive protein (CRP), ferritin, hemoglobin, and *Bifidobacterium adolescentis*. In some embodiments, the methods can result in reduction in serum inflammatory markers, leading to patency of hemodialysis access including arteriovenous fistula or a graft. In some embodiments, the methods can result in reduction of risk of peritonitis in the subject on peritoneal dialysis by improving intestinal barrier function.

DETAILED DESCRIPTION

The following description sets forth exemplary embodiments of the present technology. It should be recognized, however, that such description is not intended as a limitation on the scope of the present disclosure but is instead provided as a description of exemplary embodiments.

The instant inventor has made the unexpected discovery that complex oligosaccharides derived from mammalian milk can reduce constipation, reduce inflammation from reduction in gut-derived uremic toxins, and improve the gut microbiome (e.g., select for commensal bacteria such as *Bifidobacterium adolescentis*). Such complex oligosaccharides, it is contemplated, can improve nutrition (e.g., albumin) and correct other deficiencies (e.g., anemia) that are worsened by inflammation.

In accordance with one embodiment of the present disclosure, therefore, provided is a composition that includes one or more oligosaccharides. The one or more oligosaccharides are preferably derived from mammalian milk, plant milk, or fruit milk. In some embodiments, the oligosaccharides may be obtained from other sources or synthesized, without limitation.

Also provided, in one embodiment, is a method for improving the consistency of a subject's bowel movements, a method for reducing inflammation, a method for improving nutrition, a method for reducing constipation, and/or a method for improving gut microbiome. In some embodiments, the method entails administering to the subject an effective amount of a composition comprising one or more oligosaccharides.

Oligosaccharides (OS) are carbohydrates that contain 3 to 10 monosaccharides covalently linked through glycosidic bonds. Human milk contains approximately 7 g of carbohydrates per 100 ml, 90% being lactose, the rest being oligosaccharides. The following principal components (monomers) of oligosaccharides are found in human milk: D-glucose (Glc), D-galactose (Gal), N-acetylglucosamine (GlcNAc), L-fucose (Fuc), N-acetyl neuraminic acid (NeuAc), and N-glycolylneuraminic acid (NeuGc). These components combine in different ways to form 130 different oligosaccharides.

Examples of oligosaccharides found in various types of milk include, without limitation, a-2'-fucosyl-lactose (2'FL), a-3'-galactosyl-lactose (α-3'GL), 3'-galactosyllactose (β-3'GL), 6'-galactosyllactose (β6'GL), Fucosyl-Lactosamine, 3'-N-acetylneuraminyllactose (3'-SL), 6'-N-acetylneuraminyllactose (6'-SL), 6'-N-glycolylneuraminyllactose (6'-SL-NGc/NGL), 6'-Sialyl-lactosamine-glycolyl-Neura (6'-SLN/6'-SLacNAc), Diasylyl-Lactose (DSL), Nacetylglucosaminyl-lactose (NAL), Glycolyl-neuramyl-lactosamine, N-acetyl-glucosaminylhexosyl-lactose (NAHL), N-Di-N-acetyl-glucosaminyl-lactose (DNAL), 3'-Sialyl-6'-galactosyllactose (3-SHL), 6'-Sialyl-6'-galactosyl-lactose (6-SHL), N-Glycolyl-neuraminyl-hexosyllactose (SNGHL), Sialyl-N-acetylglucosaminyl-lactose, Lacto-N- fuco-pentaose III (LNFPIII), Lacto-N-fuco-pentaose V (LNFPIV), N-Acetyl-glucosaminyl-dihexosyl-lactose (NADHL), Nglycolyl-neuraminyl-lactose (DNGL), Sialyl-dihexasyl-lactose (SDHL), and Lacto-N-hexaose (LNH). In some embodiments, any of these is suitable for inclusion in the presently disclosed composition.

In some embodiments, the oligosaccharides include 2'-fucosyllactose (2'-FL), 3'-sialyllactose (3'-SL), 6'-sialyllactose (6'-SL), Lacto-N-neotetraose, Lacto-N-tetraose, monofucosyllacto-N-hexaose, lacto-N-neotetraose (LNnT) and various Lacto-N-fucopentaose (LNFP) species, such as LNFP I, LNFP II, LNFP III, and LNFP IV.

In some embodiments, the composition administered daily to the subject includes from 0.1 gram to 20 grams of the oligosaccharides. In some embodiments, the daily amount administered is at least 0.2 g, 0.3 g, 0.4 g, 0.5 g, 0.6 g, 0.7 g, 0.8 g, 0.9 g, 1 g, 1.5 g, 2 g, 2.5 g, 3 g, 3.5 g, 4 g, 4.5 g, 5 g, 6 g, 7 g, 8 g, 9 g, 10 g, 11 g, 12 g, 15 or 20 g. In some embodiments, the daily amount administered is not greater than 20 g, 19 g, 18 g, 17 g, 16 g, 15 g, 14 g, 13 g, 12 g, 11 g, 10 g, 9 g, 8 g, 7 g, 6 g, 5 g, 4 g, or 3 g. In some embodiments, the daily amount of the composition is 0.1-20 g, 0.5-10 g, 1-8 g, 2-6 g, or 3-5 g, without limitation.

In some embodiments, the 2'-FL administered daily to the subject includes from 0.1 gram to 20 grams of the 2'-FL. In some embodiments, the daily amount administered is at least 0.2 g, 0.3 g, 0.4 g, 0.5 g, 0.6 g, 0.7 g, 0.8 g, 0.9 g, 1 g, 1.5 g, 2 g, 2.5 g, 3 g, 3.5 g, 4 g, 4.5 g, 5 g, 6 g, 7 g, 8 g, 9 g, 10 g, 11 g, 12 g, 15 or 20 g. In some embodiments, the daily amount administered is not greater than 20 g, 19 g, 18 g, 17 g, 16 g, 15 g, 14 g, 13 g, 12 g, 11 g, 10 g, 9 g, 8 g, 7 g, 6 g, 5 g, 4 g, or 3 g. In some embodiments, the daily amount of 2'-FL is 0.1-20 g, 0.5-10 g, 1-8 g, 2-6 g, or 3-5 g, without limitation.

In some embodiments, the composition does not include other components of mammalian milk, or other oligosaccharides of the mammalian milk. In some embodiments, the composition includes limited amount of other components or other oligosaccharides of the mammalian milk In some embodiments, less than 10% of the oligosaccharides in the composition are 3'-SL. In some embodiments, less than 9%, 8%, 7%, 6%, 5%, 4%, 3%, 2%, 1%, 0.5%, 0.2%, 0.1%, or 0.01% of the oligosaccharides in the composition are 3'-SL.

In some embodiments, less than 10% of the oligosaccharides in the composition are 6'-SL. In some embodiments, less than 9%, 8%, 7%, 6%, 5%, 4%, 3%, 2%, 1%, 0.5%, 0.2%, 0.1%, or 0.01% of the oligosaccharides in the composition are 6'-SL.

In some embodiments, less than 10% of the oligosaccharides in the composition are Lacto-N-neotetraose. In some embodiments, less than 9%, 8%, 7%, 6%, 5%, 4%, 3%, 2%, 1%, 0.5%, 0.2%, 0.1%, or 0.01% of the oligosaccharides in the composition are Lacto-N-neotetraose.

In some embodiments, less than 10% of the oligosaccharides in the composition are Lacto-N-tetraose. In some embodiments, less than 9%, 8%, 7%, 6%, 5%, 4%, 3%, 2%, 1%, 0.5%, 0.2%, 0.1%, or 0.01% of the oligosaccharides in the composition are Lacto-N-tetraose.

In some embodiments, less than 10% of the oligosaccharides in the composition are monofucosyllacto-N-hexaose. In some embodiments, less than 9%, 8%, 7%, 6%, 5%, 4%, 3%, 2%, 1%, 0.5%, 0.2%, 0.1%, or 0.01% of the oligosaccharides in the composition are monofucosyllacto-N-hexaose.

In some embodiments, less than 10% of the oligosaccharides in the composition are LNnT. In some embodiments, less than 9%, 8%, 7%, 6%, 5%, 4%, 3%, 2%, 1%, 0.5%, 0.2%, 0.1%, or 0.01% of the oligosaccharides in the composition are LNnT.

In some embodiments, less than 10% of the oligosaccharides in the composition are LNFP. In some embodiments, less than 9%, 8%, 7%, 6%, 5%, 4%, 3%, 2%, 1%, 0.5%, 0.2%, 0.1%, or 0.01% of the oligosaccharides in the composition are LNFP.

In some embodiments, at least 10% of the oligosaccharides in the composition are 2'-FL. In some embodiments, at least 15%, 20%, 25%, 30%, 35%, 40%, 45%, 50%, 55%, 60%, 65%, 70%, 75%, 80%, 85%, 90%, 95%, 98%, or 99% of the oligosaccharides in the composition are LNFP.

When the oligosaccharides are obtained from milk, in some embodiments, certain other components in the milks are removed. In some embodiments, therefore, the composition does not include certain amount of protein, fiber, or fat. The following table lists some major components of various types of milk.

TABLE 1

Major components of milk from different sources

| Nutrient (per 100 mL) | Cow milk (whole) | Soy milk (calcium added) | Almond milk | Oat milk | Human milk |
|---|---|---|---|---|---|
| Protein (g) | 3.2 | 2.9 | 0.64 | 1.2 | 1.1 |
| Fat (g) | 3.3 | 1.6 | 1.2 | 2.1 | 4.2 |
| Carbohydrates (g) | 4.8 | 1.7 | 0.63 | 6.6 | 7.5 |
| Calcium (mg) | 114 | 124 | 212 | 144 | 30 |
| Potassium (mg) | 133 | 120 | 72 | 160 | 55 |
| Sodium (mg) | 43 | 37 | 77 | 58 | 15 |
| Cholesterol (mg) | 10 | 0 | 0 | 0 | 14 |

In some embodiments, the composition includes less than about 1% w/v of proteins. In some embodiments, the solution includes less than about 0.9%, 0.8%, 0.7%, 0.6%, 0.5%, 0.4%, 0.3%, 0.2%, 0.15%, 0.1%, 0.05%, 0.02%, 0.01%, 0.005%, or 0.001% w/v of proteins.

In some embodiments, the composition includes less than about 1% w/v of fat (or lipids). In some embodiments, the solution includes less than about 0.9%, 0.8%, 0.7%, 0.6%, 0.5%, 0.4%, 0.3%, 0.2%, 0.15%, 0.1%, 0.05%, 0.02%, 0.01%, 0.005%, or 0.001% w/v of fat (or lipids).

In some embodiments, the composition includes less than about 1% w/v of cholesterol. In some embodiments, the solution includes less than about 0.9%, 0.8%, 0.7%, 0.6%, 0.5%, 0.4%, 0.3%, 0.2%, 0.15%, 0.1%, 0.05%, 0.02%, 0.01%, 0.005%, or 0.001% w/v of cholesterol.

The composition can further include other nutrients, sugars (e.g., sucrose, glucose, and fructose), proteins, amino acids, vitamins (e.g., vitamin C, B, K or E), stevia, monk fruit, citric acid, and flavoring agents (e.g., lime and orange).

The composition may be a solution or a solid composition. In some embodiments, the solid composition can be obtained by drying the solution of the present disclosure. In other embodiments, the solid compositions may be in the form of powders, granules, tablets, caplets, capsules, pills, suspensions, and solutions, without limitation.

As noted, the present compositions and methods can bring various benefits, such as improving the consistency of a subject's bowel movements, reducing inflammation, improving nutrition, reducing constipation, and/or improving gut microbiome.

In some embodiments, the subject being treated by the method suffers from constipation. In some embodiments, the method results in reduction of constipation in the subject.

In some embodiments, the subject being treated has a chronic kidney disease. In some embodiments, the subject being treated has an end stage renal disease. In some embodiments, the subject being treated is on dialysis, such as peritoneal dialysis or hemodialysis.

The administration can be carried out daily, every other day, once every 3 days, 4 days, 5 days, 6 days, every week, every two weeks, without limitation. In some embodiments, the administration is carried out for at least 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 3 months, 4 months, 5 months, 6 months, 7 months, 8 months, 9 months, 10 months, 11 months, or 12 months.

In some embodiments, the treatment results in an improvement in nutrition or inflammation markers, such as serum albumin, C-reactive protein (CRP), ferritin, hemoglobin, and *Bifidobacterium adolescentis*. In some embodiments, the treatment results in reduction in serum inflammatory markers, leading to patency of hemodialysis access including arteriovenous fistula or a graft. In some embodiments, the treatment results in reduction of risk of peritonitis in the subject on peritoneal dialysis by improving intestinal barrier function.

EXAMPLES

The following examples are included to demonstrate specific embodiments of the disclosure. It should be appreciated by those of skill in the art that the techniques disclosed in the examples which follow represent techniques to function well in the practice of the disclosure, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the disclosure.

Example 1. HMO Treatment of Patients with ESRD on Hemodialysis with Constipation Five subjects with ESRD on hemodialysis with constipation were treated with 2'-FL (3.3 grams/day) for 12 weeks.

Generally, treatment resulted in improvement in bowel movement consistency (from hard stool to soft) and regularity (on average, bowel movements increased from one bowel movement every other day to one bowel movement every day).

Meanwhile, nutrition, hemoglobin, and inflammatory biomarkers were measured in each of the these patients at each month during the treatment. The results are presented in Table 2.

TABLE 2

Measurement of Nutrition, Hemoglobin, and Inflammatory Biomarkers After 12 Week HMO Treatment In Patients With ESRD On Hemodialysis With Constipation

| Patient 1 | | | | |
|---|---|---|---|---|
| Month of treatment | 0 | 1 | 2 | 3 |
| Ferritin(ng/ml) | 548 | 546 | 503 | 364 |
| CRP (mg/L) | | 0.7 | 0.5 | 0.3 |
| Hg (g/dl) | 10.6 | 10.5 | 11.2 | 10.7 |
| Albumin (g/dl) | 3.6 | 3.7 | 3.8 | 3.5 |

TABLE 2-continued

Measurement of Nutrition, Hemoglobin, and Inflammatory Biomarkers After 12 Week HMO Treatment In Patients With ESRD On Hemodialysis With Constipation

| Patient 2 | | | | |
|---|---|---|---|---|
| Month of treatment | 0 | 1 | 2 | 3 |
| Ferritin(ng/ml) | 1250 | 1188 | 1000 | 899 |
| CRP (mg/L) | | 6.2 | 4.3 | 2.3 |
| Hg (g/dl) | 11.2 | 11.3 | 10.6 | 10.2 |
| Albumin (g/dl) | 4.2 | 4.3 | 4.2 | 4.2 |

| Patient 3 | | | | |
|---|---|---|---|---|
| Month of treatment | 0 | 1 | 2 | 3 |
| Ferritin(ng/ml) | 1243 | 1135 | 827 | 907 |
| CRP (mg/L) | | 19 | 1.9 | 1.6 |
| Hg (g/dl) | 10.5 | 11.3 | 10.9 | 11.2 |
| Albumin (g/dl) | 3.9 | 4 | 3.9 | 4 |

| Patient 4 | | | | |
|---|---|---|---|---|
| Month of tx | 0 | 1 | 2 | 3 |
| Ferritin (ng/ml) | 1487 | 1208 | 749 | 985 |
| CRP(mg/L) | | 2 | 1.5 | 1.5 |
| Hg (g/al) | 10.8 | 10.5 | 11.3 | 11.4 |
| Albumin (g/dl) | 3.9 | 3.9 | 3.9 | 3.8 |

| Patient 5 | | | | |
|---|---|---|---|---|
| Month of treatment | 0 | 1 | 2 | 3 |
| Ferritin(ng/ml) | 580 | 431 | 313 | 332 |
| CRP (mg/L) | | 27.5 | 28 | 12.4 |
| Hg (g/dl) | 12.2 | 12.6 | 12.2 | 12 |
| Albumin (g/dl) | 4.1 | 4.1 | 3.9 | 3.8 |

In addition to improvement in constipation, as shown in Table 2, average laboratory parameters showed a significant and persistent reduction in serum inflammatory markers including ferritin and CRP (C-reactive protein) levels as well as an improvement or stabilization in nutrition (albumin) and anemia (hemoglobin). It is worth noting that in month 3, the rise in ferritin correlated with IV iron infusion, not from rise in inflammation as CRP in those subjects in week 12 did not rise.

Both of these findings are unexpected. Normally, HMOs are typically active in the distal colon where they serve as the food for commensal (beneficial) bacteria. HMOs also have a protective role in maintaining intestinal cell barrier function. However, it was unclear if HMOs, such as 2'-FL, can be absorbed in the bloodstream in amounts significant enough to reduce systemic inflammation as measured by inflammatory markers such as CRP and ferritin. Also, it was unclear whether such an action is through its change in the gut microbiome that can influence the amount of gut-derived toxins that circulate systemically.

This example demonstrates that HMOs can be useful in preservation of dialysis access (arteriovenous fistulas/grafts) patency which are often lost due to thrombosis largely from an inflammatory milieu prevalent in end stage renal disease.

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Thus, for example, the terms "comprising," "including," "containing," etc., shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and sub-generic groupings falling within the generic disclosure also form part of the invention. This includes the generic description of the invention with a proviso or a negative limitation removing any subject matter from the genus, regardless of whether or not the excised materials is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions will control.

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

The invention claimed is:

1. A method for improving gastrointestinal function in a subject having chronic kidney disease, comprising administering to the subject an effective amount of a composition comprising oligosaccharides, wherein at least 20% of the oligosaccharides are 2'-fucosyllactose (2'-FL).

2. The method of claim 1, wherein the 2'-FL is synthetic.

3. The method of claim 1, wherein at least 50% of the oligosaccharides are 2'-FL.

4. The method of claim 1, wherein at least 75% of the oligosaccharides are 2'-FL.

5. The method of claim 1, wherein from 0.1 g to 20 g of 2'-FL is administered to the subject each day.

6. The method of claim 1, wherein from 1 g to 5 g of 2'-FL is administered to the subject each day.

7. The method of claim 1, wherein the composition further comprises an additive selected from the group consisting of sugars, proteins, amino acids, lipids, electrolytes, and vitamins and combinations thereof.

8. The method of claim 1, wherein the oligosaccharides further comprise 3'-sialyllactose (3'-SL), 6'-sialyllactose (6'-SL), Lacto-N-neotetraose, Lacto-N-tetraose, monofucosyl-lacto-N-hexaose, Lacto-N-fucopentaose (LNFP), lacto-neo-tetraose (LNnT), or a combination thereof.

9. The method of claim 1, wherein the subject has an end stage renal disease.

10. The method of claim 1, wherein the subject is on peritoneal dialysis or hemodialysis.

11. The method of claim 10, wherein the composition is administered to the subject for at least 2 weeks.

12. The method of claim 10, wherein the administration results in an improvement in nutrition or inflammation markers of chronic kidney disease.

13. The method of claim 12, wherein the markers are selected from the group consisting of serum albumin, C-reactive protein (CRP), ferritin, hemoglobin, and bifidobacterium.

14. The method of claim 10, wherein the administration results in reduction in serum inflammatory markers, leading to patency of hemodialysis access.

15. The method of claim 10, wherein the administration results in reduction of risk of peritonitis in the subject on peritoneal dialysis by improving intestinal barrier function.

* * * * *